US010610652B2

(12) United States Patent
Zhang et al.

(10) Patent No.: US 10,610,652 B2
(45) Date of Patent: Apr. 7, 2020

(54) METHOD AND DEVICE FOR COLLABORATING VENTILATION USING EXTERNAL DIAPHRAGM PACEMAKER AND VENTILATOR

(71) Applicant: Hongxuan Zhang, Guangzhou (CN)

(72) Inventors: Hongxuan Zhang, Guangzhou (CN); Jialiang Chen, Guangzhou (CN); Wenfeng Zhan, Guangzhou (CN); Yili Mao, Guangzhou (CN); Miao Chen, Guangzhou (CN)

( * ) Notice: Subject to any disclaimer, the term of this patent is extended or adjusted under 35 U.S.C. 154(b) by 1030 days.

(21) Appl. No.: 14/441,515

(22) PCT Filed: Sep. 27, 2013

(86) PCT No.: PCT/CN2013/084435
§ 371 (c)(1),
(2) Date: May 8, 2015

(87) PCT Pub. No.: WO2014/071785
PCT Pub. Date: May 15, 2014

(65) Prior Publication Data
US 2015/0283340 A1 Oct. 8, 2015

(30) Foreign Application Priority Data
Nov. 9, 2012 (CN) .......................... 2012 1 0448912

(51) Int. Cl.
*A61M 16/00* (2006.01)
*A61N 1/36* (2006.01)
(Continued)

(52) U.S. Cl.
CPC .... *A61M 16/0003* (2014.02); *A61M 16/0051* (2013.01); *A61N 1/3601* (2013.01);
(Continued)

(58) Field of Classification Search
None
See application file for complete search history.

(56) References Cited

U.S. PATENT DOCUMENTS 5,174,287 A * 12/1992 Kallok ................. A61N 1/3601
128/200.24
6,360,740 B1 * 3/2002 Ward .................... A61N 1/3601
128/200.24

(Continued)

*Primary Examiner* — Rachel T Sippel
(74) *Attorney, Agent, or Firm* — JCIPRNET

(57) ABSTRACT

The present invention discloses a method for synchronized ventilation using an external diaphragm pacemaker and a ventilator, which includes the following steps: (1) filtrating captured EAdi signal to reduce the noises, (2) assessing the absolute peak value a of the EAdi signal and: if a<0.5 μV, adjust the external diaphragm pacemaker to issue a stimulus current at a frequency of 10-12 beats per minute, and at the same time trigger the ventilator to perform ventilation in an assisted ventilation mode; if 0.5≤a≤1.0 μV, adjust the external diaphragm pacemaker to issue a stimulus current at a frequency of 5-8 beats per minute, and at the same time trigger the ventilator to perform ventilation in an assisted ventilation mode; if 1.0<a≤2.0 μV, adjust the external diaphragm pacemaker to issue a stimulus current at a frequency of 3-4 beats per minute and at the same time trigger the ventilator to perform ventilation in an assisted ventilation mode. The present invention also discloses a device which couples an external diaphragm pacemaker to a ventilator. The present invention brings the external diaphragm pacemaker into the application of mechanical ventilation in the emergency room and intensive care unit.

14 Claims, 4 Drawing Sheets

(51) Int. Cl.
*A61N 1/362* (2006.01)
*A61N 1/365* (2006.01)
(52) U.S. Cl.
CPC ......... *A61N 1/365* (2013.01); *A61N 1/36014* (2013.01); *A61N 1/3625* (2013.01); *A61M 2205/33* (2013.01); *A61M 2205/3303* (2013.01); *A61M 2205/50* (2013.01); *A61M 2205/502* (2013.01); *A61M 2210/1014* (2013.01); *A61M 2230/04* (2013.01); *A61M 2230/60* (2013.01)

(56) References Cited

U.S. PATENT DOCUMENTS

| | | | | |
|---|---|---|---|---|
| 2008/0161878 | A1* | 7/2008 | Tehrani | A61N 1/3601 607/42 |
| 2008/0287820 | A1* | 11/2008 | Ignagni | A61N 1/3601 600/529 |
| 2010/0094376 | A1* | 4/2010 | Penner | A61N 1/0517 607/42 |
| 2010/0185253 | A1* | 7/2010 | Dimarco | A61N 1/0553 607/42 |
| 2011/0190845 | A1* | 8/2011 | Weisfeldt | A61B 5/04001 607/42 |
| 2012/0035452 | A1* | 2/2012 | Jalde | A61B 5/04884 600/380 |
| 2014/0123979 | A1* | 5/2014 | Doyle | A61M 16/0057 128/204.23 |

* cited by examiner

METHOD AND DEVICE FOR COLLABORATING VENTILATION USING EXTERNAL DIAPHRAGM PACEMAKER AND VENTILATOR

FIELD OF THE INVENTION

The present invention relates to a method and device for collaborating ventilation using an external diaphragm pacemaker coupled with a mechanical ventilator.

BACKGROUND OF THE INVENTION

Mechanical ventilation has saved countless lives for those patients suffered with respiratory failures in emergency or under ICU. However, it is a double-edged sword which, at meantime of saving lives, may also cause injuries, such as, ventilator-induced lung injury (or VILI), ventilator-associated pneumonia (or VAP), ventilator-induced diaphragmatic dysfunction (or VIDD) and the like. VIDD refers generally to any injuries induced by mechanical ventilation in the form of diaphragmatic weakness and diaphragm muscle atrophy, resulting in a significant reduction in respiratory capacity and reliance on the breathing machine for breathing. Diaphragmatic function is a key factor to consider in determining whether patients receiving mechanical ventilation can successfully withdraw from the breathing machine. Evidence shows that VIDD is very common in mechanically ventilated patients and causes difficulties in weaning patients. Clinical weaning failure rate is 24%-29%, of which 31% will face a high risk of death. It often necessities extended stays in the intensive care unit, thus extra burdens on healthcare resources of the society and increased medical fees to patients.

As in the field of intensive care unit (referred to as ICU), VILI and VAP caught attentions a long time ago and experts in the field have long been committed to addressing some of the symptoms but the efforts are nonetheless mainly confined to the improvement and adjustment of the operating mode of the ventilator for the purpose of reducing the incidence of VILI. To deal with VAP, the measures are through enhanced care, reduction in infection and timely use of sufficient doses of anti-infection medicines. However, it is only until recent years when attentions are paid to VIDD and therefore there are presently no effective clinical means in preventing and treating VIDD. The usual clinical measure is through medicines, mainly antioxidants such as vitamin E, calpain/cathepsin inhibitors, high-dose corticosteroids, etc. The results are not very certain and some may even be toxic or have no effect at all.

The diaphragm is located between the thoracic cavity and abdominal cavity, being a wide, flat, upward bulging, dome-shaped thin structure of muscle. It is the most important muscle for the breathing function and among all participating muscles its role in the respiratory function accounts for 60%-80%. For respiration of a stationary subject, the diaphragm plays the leading role, and provides the main source of the respiratory pump function. Muscle fibers of the diaphragm can be divided into the following types: Type I is chronic contractile fatigue resistant fibers; Type IIa is rapid contraction fatigue resistant fibers and Type IIb is rapid contraction fatigue fibers. The diaphragm differs from the skeletal muscle in general as it contentiously performs rhythmic contractions with a high contraction ratio, i.e., contraction period/contraction period+relaxation period. If the contractile activity stops, even if only for a few hours, it can cause injuries to the diaphragm and reduce its contracting capability Studies found that lung cancer patients in the process of cancer surgery can suffer injuries in the diaphragm when, due to anesthesia, mechanical ventilation was used for more than 4 hours, as determined from the diaphragm biopsy taken at the same time as the cancer surgery is conducted. In other words, when a human under mechanical ventilation for a period of time, it stops all activities of the respiratory muscles including the diaphragm and causes the diaphragm disuse, resulting in diaphragm muscle fiber damage, muscle atrophy, muscle fiber remodeling, or abnormal excitation-contraction coupling, i.e., VIDD. Furthermore, the degree of injury to the diaphragm depends on the length of the period when mechanical ventilation is used.

Phrenic nerve, originating from the cervical nerves (C3-C5), is responsible for maintaining the respiratory function. It plays an important role in maintaining a normal respiratory function. Normal breathing activity starts with a nerve impulse sent by the central nervous system and transmitted along the phrenic nerve to arrive at the joint between the nerve endplate and the diaphragm, where it activates chemically-gated channel in muscle fiber membranes, causes $Na^+$ influx and $K^+$ efflux, and forms an endplate potential. The endplate potential transmits along the muscle fiber membrane for short distances with an ability of temporal and spacial summation. When the sum of the potential reaches a threshold for muscle fiber contraction, an action potential is generated by which the nerve impulse is turned into an electrical signal, triggering the diaphragmatic contraction to complete inhale action.

Diaphragmatic pacemaker (or diaphragm pacing, DP) is a medical device used to stimulate the phrenic nerve by electrical impulses, causing continuous and rhythmic muscle contractions of the diaphragm which constitute a regular breathing activity mimicking that under physiological conditions.

DP can be the implant type or external type, depending on the location where it is used. The implant type DP, as it requires being implanted in the human body by thoracotomy or VATS electrode implantation, is suitable mainly for long-term ventilation support. Presently, the implant type diaphragmatic pacemaker is difficult to be popularized in China. The external type DP (or external diaphragm pacemaker EDP, which is the type of the DP device relevant to the present invention) is a device which places the pacing electrode on the neck skin to stimulate the most superficial parts of the phrenic nerve beneath the skin. As it avoids surgery and nerve endings being cut-off, it reduces the risk of damaging the phrenic nerve. The external DP has the advantages: simple in structure, convenient to operate, non-invasive, etc., and is a technique for improving the lung ventilation and increasing the activity of the diaphragm. It is mainly used in rehabilitation exercise for patents with chronic obstructive pulmonary disease (i.e., COPD), as short-term supplementary treatments in regular intermittent: 2-3 times in 24 hours, about 30-40 minutes each time. Longer period of electrical stimulation of the phrenic nerve will not help the diaphragmatic function in rehabilitation therapy, and may very easily lead to diaphragmatic fatigue.

The existing external diaphragm pacemaker has not yet, on the level of bio-electrophysiology, attained the capability of intelligently matching with the functional movement state of the diaphragm, and can not be used in conjunction with existing mechanical ventilation methods. Therefore, such diaphragmatic pacemaker has never been used in the treatment of critically ill patients.

The foregoing described process of turning phrenic nerve impulses into electrical signals to trigger contraction of the diaphragm to complete inhale action is referred to as the electrical activity of the diaphragm, or EAdi. EAdi is nerve impulses transmitted to the diaphragm and is the best indicator of neural respiratory events. The existing technology has already achieved the capability of capturing EAdi via electrodes placed in the esophagus and using EAdi to control mechanical ventilation, such as that disclosed in Chinese Patent 200410051035.4 ("Method of starting ventilator using EAdi from an esophageal electrode"). This technology, although having improved man-machine synchronization and reduced man-machine confrontation, cannot however effectively solve the problem of VIDD because it is incapable of improving the situation of diaphragmatic dysfunction.

SUMMARY OF THE INVENTION

An object of the present invention is to provide a method of collaborative applications of an external diaphragm pacemaker with a ventilator, and introduce the external diaphragm pacemaking into application in mechanical ventilation of the emergency room and intensive care unit, in order to allow the diaphragm to get more involved in the process of mechanical ventilation and to mitigate diaphragmatic injuries induced by positive pressure ventilation.

Another object of the present invention is to provide a device that couples external diaphragm pacemaking to mechanical ventilation for applying the method described above.

The first object of the present invention is achieved by the following technical scheme:

A method of mechanic ventilation collaborated by in vitro diaphragm pacemaking, comprising the steps of:

(1) filtrating captured EAdi signal, which are mixed with interfering signals, to reduce the noises thereof and results in processed EAdi signal.

(2) performing one of the following control actions based on the absolute peak value a of the waveform of the treated EAdi signal.

(2.1) if a<0.5 µV, adjust the external diaphragm pacemaker to issue a stimulus current at a frequency of 10-12 beats per minute, and at the same time trigger the ventilator to perform ventilation in the assisted ventilation mode.

(2.2) if 0.5≤a≤1.0 µV, adjust the external diaphragm pacemaker to issue a stimulus current at a frequency of 5-8 beats per minute, and at the same time trigger the ventilator to perform ventilation in the assisted ventilation mode.

(2.3) if 1.0≤a≤2.0 µV, adjust the external diaphragm pacemaker to issue a stimulus current at a frequency of 3-4 beats per minute and at the same time trigger the ventilator to perform ventilation in the assisted ventilation mode.

(2.4) if failure to capture any diaphragmatic EAdi signal, trigger the ventilator to perform ventilation in the controlled ventilation mode (i.e., the ventilator performing, according to preset parameters, backup ventilation function), while adjusting the external diaphragm pacemaker to issue stimulus current at a frequency of 6-8 beats per minute.

The mode and operation of the assisted ventilation mode of the ventilator mentioned in steps 2.1-2.3 and the controlled ventilation mode in step (2.4) are well known in the art. The assisted ventilation mode includes the following specific modes: synchronized intermittent mandatory ventilation (SIMV), pressure support ventilation (PSV), continuous positive airway pressure (CPAP), and the controlled ventilation mode includes the following specific modes: volume control ventilation (VCV), pressure controlled ventilation (PCV), etc. In general, selection of a specific mode and preset of the operating parameters are decided by clinicians based on the specific circumstances.

In the above-described steps 2.1-2.3, according to the present invention, the coupled triggering of the ventilator can be a negative pressure type trigger. Specifically, when deemed necessary based on the EAdi signal, the negative pressure generator produces a preset negative pressure, which triggers the ventilator to operate in the assisted ventilation mode. As the ventilator is actually triggered by the diaphragm via EAdi, the latency of the trigger is greatly shortened in comparison with the conventional method which triggers in response to air influx.

Further improvements can be made in practicing the present invention. A strong signal of EAdi is normally followed by a number of smaller signal clutters. When a strong signal of EAdi is generated in response to the stimulus current from the diaphragm pacemaker, it is possible to include a logic assessment process in step 1 to filter out those signal clutters and eliminate their interference on diaphragm pacing. The logic assessment is performed on the interval t between peaks of two successive positive half waves (or two successive negative half waves) of the EAdi signal in real time:

(a) If t<5s, discard the signal without issuing the stimulus current nor triggering the ventilator by generating the negative pressure.

(b) if 5s≤t≤10s, return to the signal to step 2 to perform further assessment and take an action accordingly.

(c) if t>10s, treat the situation as if no EAdi signal is captured and execute the action of step 2.4

In step 1 of the present invention, the EAdi signals mixed with interfering noises can be subject to the following filtration procedures sequentially: high-pass filtration, low-pass filtration, 50 Hz power frequency interference filtration and ECG wavelet filtration.

The second object of the present invention is achieved by the following technical solution: an external diaphragm pacemaking device coupled to a ventilator, including an external diaphragm pacemaker, characterized in that: it further comprises a negative pressure generator and an EAdi acquisition module for capturing EAdi signals from the diaphragm muscle, a signal processing module for treating the EAdi signals, and a microprocessor for analysis and assessment of the EAdi signals and a microcontroller for coupling control of a ventilator. The negative pressure generator has a negative pressure generating end connected to the ventilator's terminal on the patient side. The EAdi acquisition module collects or captures the EAdi signals, which are first treated by the signal treatment module and then sent to the microprocessor for analysis and assessment. Based on the strength and time interval of two successive half-wave peaks of an EAdi signal, a corresponding control signal is sent to the microcontroller. The microcontroller outputs corresponding control signals which, on the one hand, triggers external diaphragm pacemaker into operation and, on the other hand, triggers the operation of the negative pressure generator so that a negative pressure is generated in the negative end, which in turn triggers the operation of the ventilator.

The signal processing module in the present invention comprises a signal amplifier, analog to digital converter and digital signal processor for filtering EAdi signals, being successively connected in that order. The signal from the diaphragm outputted by the EAdi acquisition module is first amplified by the signal amplifier, then undergoes conversion by the analog to digital converter, and finally filtered by the digital signal processor prior to being outputted.

Further, the apparatus according to the present invention may also be provided with a display driver circuit and a monitor for displaying the operating state of the apparatus. The microprocessor has a display signal output terminal, which is connected to the monitor via the display driver circuit.

Compared with the prior art, the present invention has the following advantageous technical effects:

(1) The present invention for the first time enables the external diaphragm pacemaker EDP be used with the ventilator in the treatment of critically ill patients in intensive care unit (ICU). It captures the EAdi signal from the patient's diaphragm, filters it, calculates the absolute peak value a, uses the analysis and assessment of the a value as the basis to control an external pacemaker to issues a stimulus current and at the same time to start the negative pressure generator to trigger the operation of a coupled ventilator, thereby realizing synchronization between in vitro diaphragm pacemaking and mechanical ventilation with patients under intensive care so that the intermittent triggering of both devices are intelligently coupled. It achieves proper stimulation on the diaphragm while providing necessary assisted ventilation according to the patient's respiration status in real time. In this way, a better man-machine synchronization is achieved, with reduced man-machine confrontation and harm on patient's respiration function and, at the same time, it allows more involvement of the diaphragm in the process of machine ventilation and reduces the pressure requirement in supporting the ventilation process so that the ventilation may proceed under a lower pressure and thus reduce injuries caused by the positive-pressure in ventilation.

(2) The invention introduces an external diaphragm pacemaker into the emergency room and intensive care unit to intelligently match machine ventilation with the diaphragm's own function. This not only helps the patient in maintaining and improving the diaphragm's function during the process of mechanical ventilation, but also has the effect of avoiding or reducing VIDD. Furthermore, the present invention broadens the scope of external diaphragm pacemaker's application and it can be used to maximize the possibility of avoiding VILI and VAP, but can now also be used to effectively prevent and treat VIDD. This provides an unprecedented solution to the problems caused by these three complications plagued ICU doctors for so many years. Additionally, it reduces the drugs to be used for avoiding VILI and VAP, which in turn reduces the side-effects and financial burdens to the patients.

(3) The present invention is applicable to patients who are under sedation anesthesia or have lost the ability of spontaneous breathing, making it possible for those patients to gradually regain the ability of spontaneous breathing.

(4) The present invention uses the negative pressure generator as the coupling mediator, achieving a universal-comparable interface and seamless connectivity. It only requires the negative pressure end of the negative pressure generator be connected to the patient end of the ventilator to trigger the operation of the ventilation machine. As such, the present invention is applicable to all existing ventilators to control ventilation timing and suitable for a wide-spread retrofit and adaptation.

BRIEF DESCRIPTION OF THE DRAWINGS

In FIG. 6, 1 refers to the ventilator's patient end; 2 refers to the negative pressure generating end of the negative pressure generator.

DETAILED DESCRIPTION OF PARTICULAR EMBODIMENTS

The present invention is further elaborated below with reference to specific embodiment.

The present invention provides a method for collaborated ventilation by a ventilator assisted by an external diaphragm pacemaker, comprises the steps detailed below.

(1) Treatment of captured EAdi signal, which are usually mixed with interfering noises, to obtain a treated EAdi signal:

The capture of EAdi signals can be conducted by using an electrode placed in the esophagus, which of course can be replaced by other EAdi capture means known in the art. The captured raw EAdi signal contains a significant amount of interfering noises. As shown in FIG. 3, an eight-channel esophageal tube bipolar electrode is used to collect weak EAdi signals, and the weak EAdi signals are first amplified and then undergo an analog-to-digital conversion. The EAdi signal, with interfering noises, is then filtered to remove the noises. The filtration is conducted successively with a high-pass filter, a low-pass filter, 50 Hz power frequency filter, and an ECG wave interference wavelet filter. These filtration processes are known in the art, such as the method disclosed in the paper entitled "Study on novel method of man-machine synchronization based on EAdi" published in "Journal of Biomedical Engineering" Vol. 6, December 2009 or the EAdi extraction and treatment method disclosed in the paper entitled "Method of EAdi noise reduction based on combination of QRS detection and wavelet threshold" published in "Chinese Journal of Biomedical Engineering" Vol. 6, December 2009. The resulting EAdi signals are then amplified 1000 times, and have a waveform shown in FIG. 2, with alternate strong waves and week waves.

Figure 1:
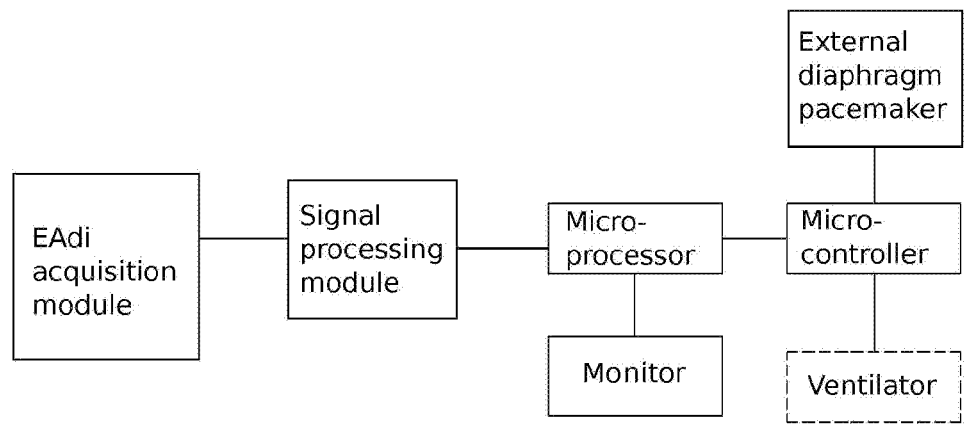
FIG. 1 is a diagram showing the connection among the components of the coupled external diaphragm pacemaker and the ventilator according to the present invention.
Figure 2:
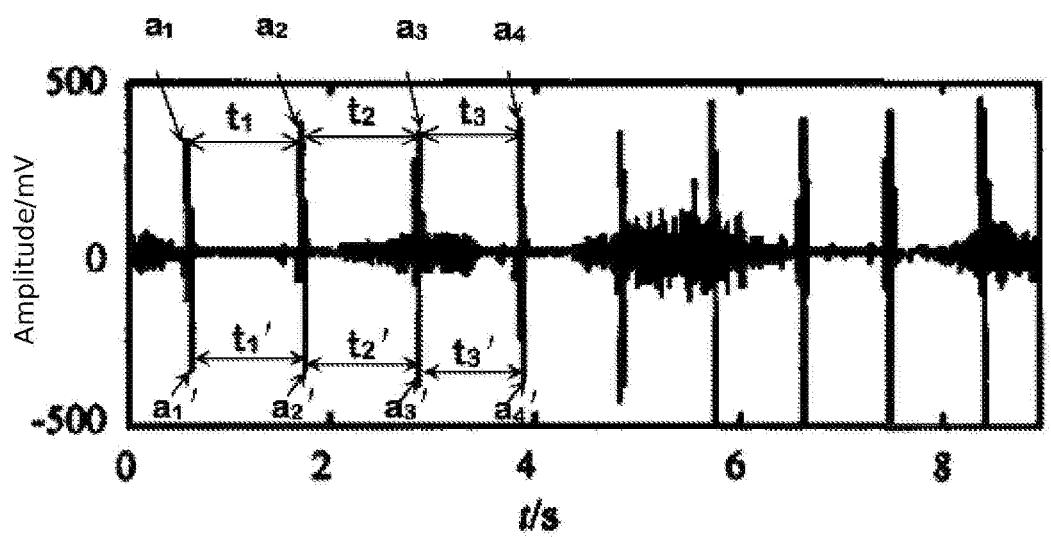
FIG. 2 is a waveform diagram of an EAdi signal after being magnified 1000 times.
Figure 3:
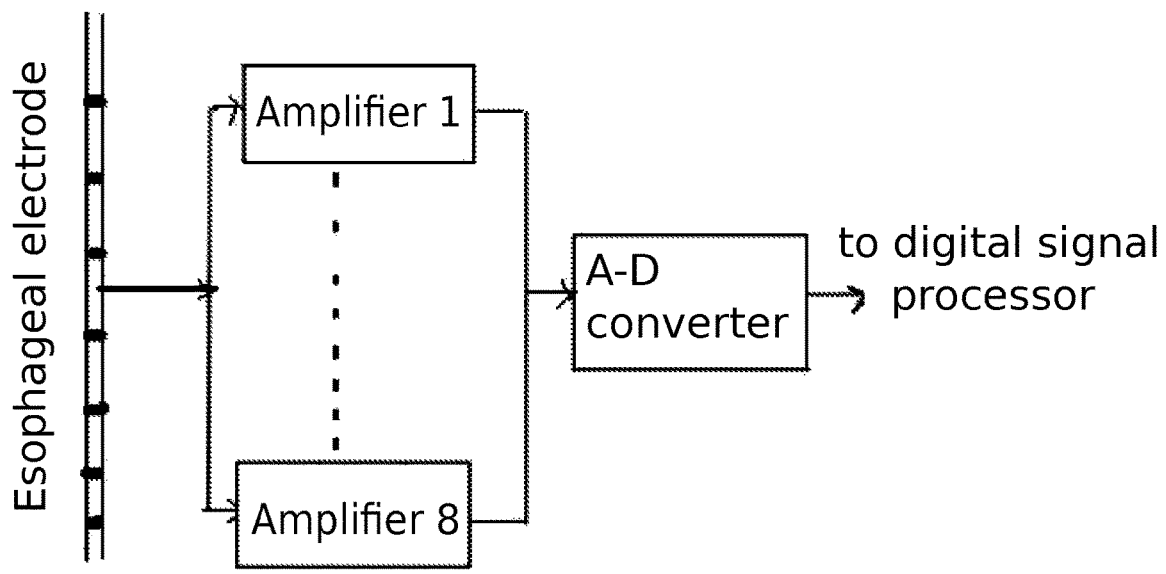
FIG. 3 is a diagram showing the connection between the EAdi acquisition module and signal processing module according to the present invention.

(2) Triggering corresponding control actions according to the assessment results on absolute peek value a, which is shown in FIG. 2 as $a_1$, $a_2$, $a_3$, $a_1'$, $a_2'$, and $a_3'$, as follows:

(2.1) if a<0.5 µV, a value indicating inability of spontaneous self diaphragm pacemaking, issue a control action to direct the external diaphragm pacemaker to send stimulus currents 10 to 12 beats per minute, while at the same time triggering the ventilator operation in an assisted ventilation mode.

(2.2) if 0.5≤a≤1.0 µV, a value indicating that external diaphragm pacemaking is necessary, issue a control action to direct the external diaphragm pacemaker to send stimulus currents 5 to 8 beats per minute, while at the same time triggering the ventilator operation in an assisted ventilation mode.

(2.3) if 1.0<a≤2.0 µV, a value indicating an ability of self-diaphragm pacemaking, issue a control action to direct the external diaphragm pacemaker to send stimulus currents 3 to 4 beats per minute, while at the same time triggering the ventilator operation an assisted ventilation mode.

(2.4) if no EAdi is captured, issue a control action directing the ventilator to operate in a controlled ventilation mode, that is, performing a backup ventilation function according to preset parameters, and at the same time directing the external diaphragm pacemarker to issue stimulus currents 6 to 8 times per minute.

After the initial current stimulation by the diaphragm pacemaker, the current stimulation continues for 30-40 minutes and then stops. Such stimulation period (30-40 minutes) repeats 2-3 times within 24 hours. During the times when the diaphragm pacemaker is not in operation, the ventilator maintains its operation according to regular operating parameters used in conventional practice in the clinic.

The assisted ventilation mode (AV) is a conventional ventilation mode known in the art. It is triggered by a pressure and an air flow, limited by capacity, and switched off by capacity. It can keep ventilator's operation collaborating with patient's own respiration, which is conducive for patient to regain the ability of spontaneous respiration. The assisted ventilation mode includes the step intermittent mandatory ventilation mode (SIMV), pressure support ventilation (PSV), continuous positive airway pressure mode (CPAP), etc. Selection of a particular assisted ventilation mode and its parameter setting is decided by the doctor according to factors under a particular clinical circumstance.

The controlled ventilation mode (CV) is a conventional ventilation mode known in the art. It is triggered by a timer and its operation is unrelated to the patient's spontaneous breathing cycles. In other words, it is a non-synchronized ventilation mode. The controlled ventilation mode includes the volume control ventilation mode (VCV) and pressure control ventilation mode (PCV). Selection of a particular controlled ventilation mode and its parameter setting is decided by the doctor according to factors under a particular clinical circumstance.

In steps (2.1) to (2.3) described above, a negative pressure can be used for a synchronized triggering of the ventilator, that is, a preset negative pressure generated by the negative pressure generator according to the assessment of the EAdi signal. The negative pressure maintains about 1 second and afterwords the ventilator can operate autonomously. The ventilator started by the negative pressure will operate in an assisted ventilation mode. In steps (2.1) to (2.3), the synchronized triggering of the ventilator to operate in the assisted ventilation mode may also be effected by the EAdi signal directly based on the result of assessment on the EAdi signal and a preset criterion.

After the diaphragm pacemaker issuing the stimulus current, the captured EAdi signal is analyzed in real time to determine the time interval t between the peeks of two successive positive half waves, which is shown in FIG. 2 as $t_1$, $t_2$, $t_3$.

(a) If t<5s, discard the signal without sending stimulus current and triggering the ventilator.

(b) if 5s≤t≤10s, turn to step (2) and determine the peak value and the action corresponding to the peak value.

(c) if t>10s, treat it as if no EAdi is captured and take the action described in step (2.4). Considering the possibility that the patient has lost the respiration ability or the sensing electrode falls off, the ventilator is switched to operate in the controlled ventilation mode, that is, the backup ventilation mode according to preset parameters in which the patient's respiration is completely replaced by the machine. In this situation, the alarm should also be triggered.

FIG. 1 and FIGS. 3-5 depict a diaphragm pacemaking device coupled to a ventilator. It comprises an external diaphragm pacemaker, a negative pressure generator for produce negative pressure in the patient end of the ventilator, an EAdi acquisition module for capturing the signals from the diaphragm, a processing module for treating the captured the EAdi signals, a microprocessor for analysis and assessment on the EAdi signals, a microcontroller for controlling synchronization. The negative pressure generator has a negative pressure generation end 2, which is connected to the patient end 1 of the ventilator. In operation, the EAdi signal is captured by the acquisition module, pre-treated by the processing module, and then analyzed and assessed by the microprocessor regarding the strength of the signal (i.e., the value of a) and the time interval between peaks of two successive positive or negative half-waves (i.e., the value of t). Based on the values of a and t, the microprocessor outputs corresponding control signals to the microcontroller. According to the received control signals, the microcontroller simultaneously triggers the operation of the external diaphragm pace maker on the one hand and the operation of the negative pressure generator on the other hand, which produces a negative pressure to trigger the operation of the ventilator.

In the above described device, the signal processing module comprises a signal amplifier, an analog-to-digital converter, and a digital signal processor. In this module, the signal output from the signal acquisition module is amplified by the amplifier, converted to the digital form and then filtered by the digital signal processor prior to be outputted.

Figure 7:
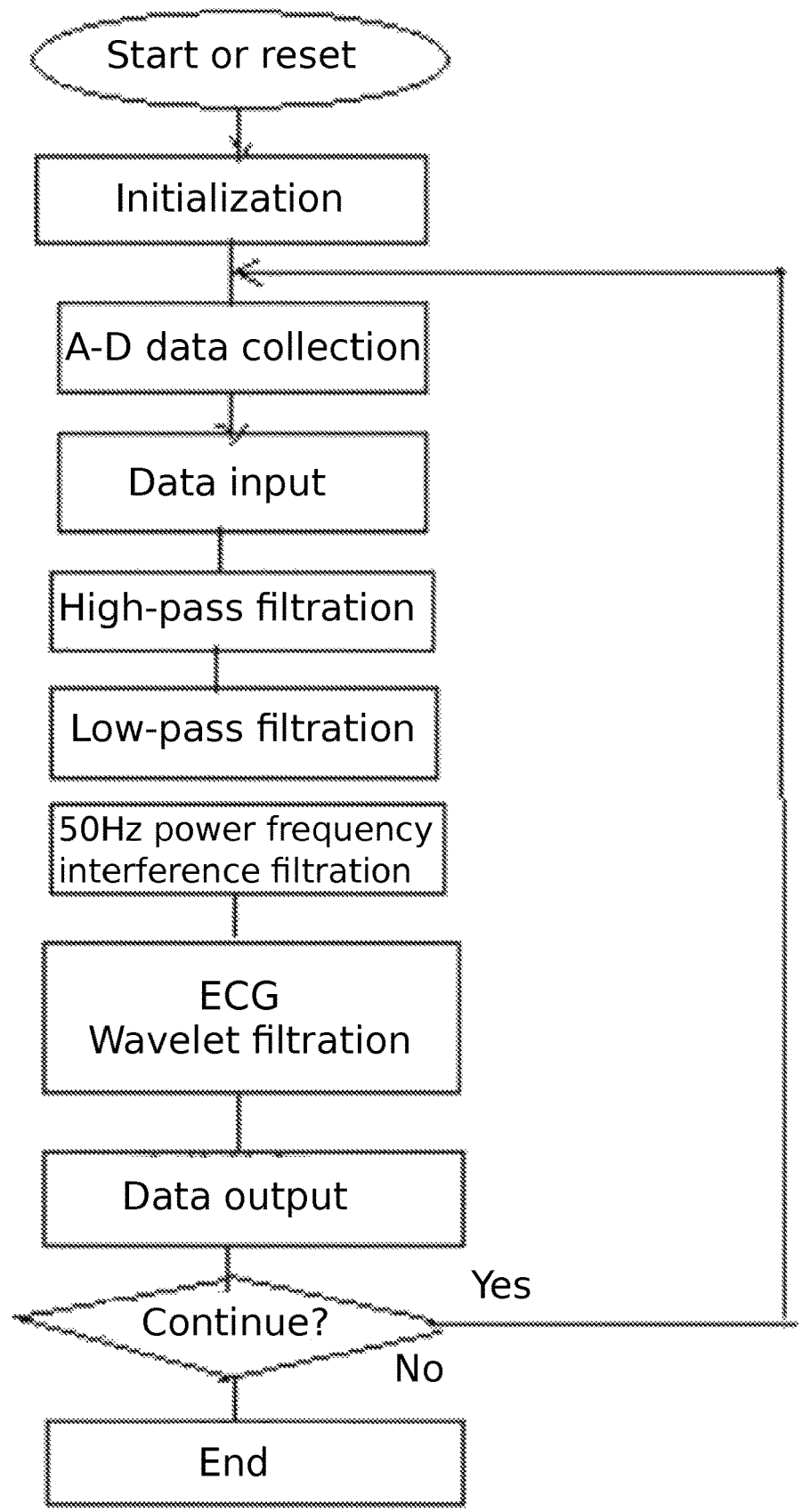
FIG. 7 is a flow chart showing the steps through which the EAdi signal is filtered for noise reduction according to the present invention.

As shown in FIG. 3, the signal acquisition module in this particular embodiment is an eight-channel esophageal tube bipolar electrode. The captured diaphragm signal is amplified by eight front placed amplifiers (1 . . . 8) (Model INA337), and sent to the analog-to-digital converter (Model AD7866A-D) for conversion. Then, the signal is filtered by the digital signal processor (Model TMS320VC5416) with a high pass filter (10 Hz), low-pass filtering (1 kHz) and wavelet filtering (for ECG interference). The flowchart of the filtering procedure is shown in FIG. 7.

Figure 4:
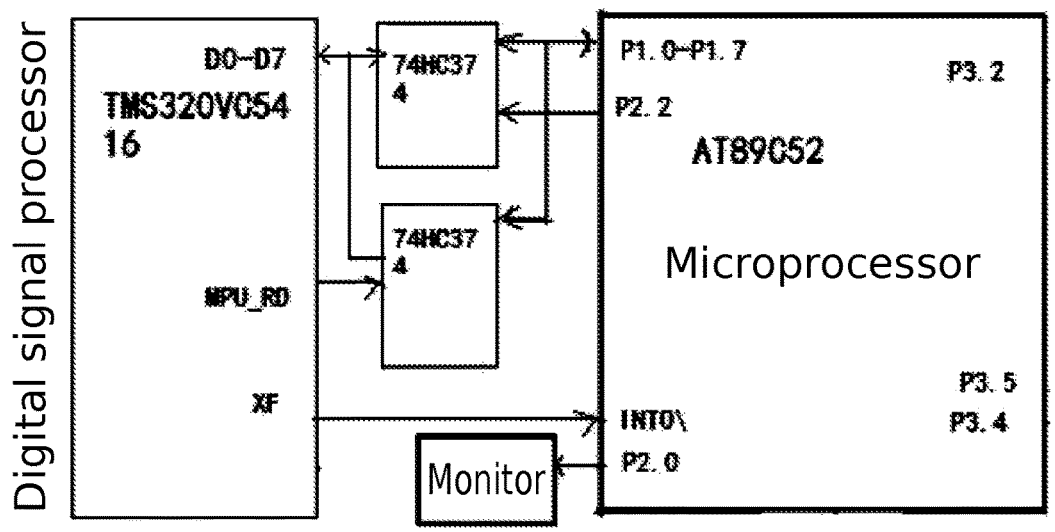
FIG. 4 is a diagram showing the connection between the digital signal processor and the microprocessor according to the present invention.
Figure 5:
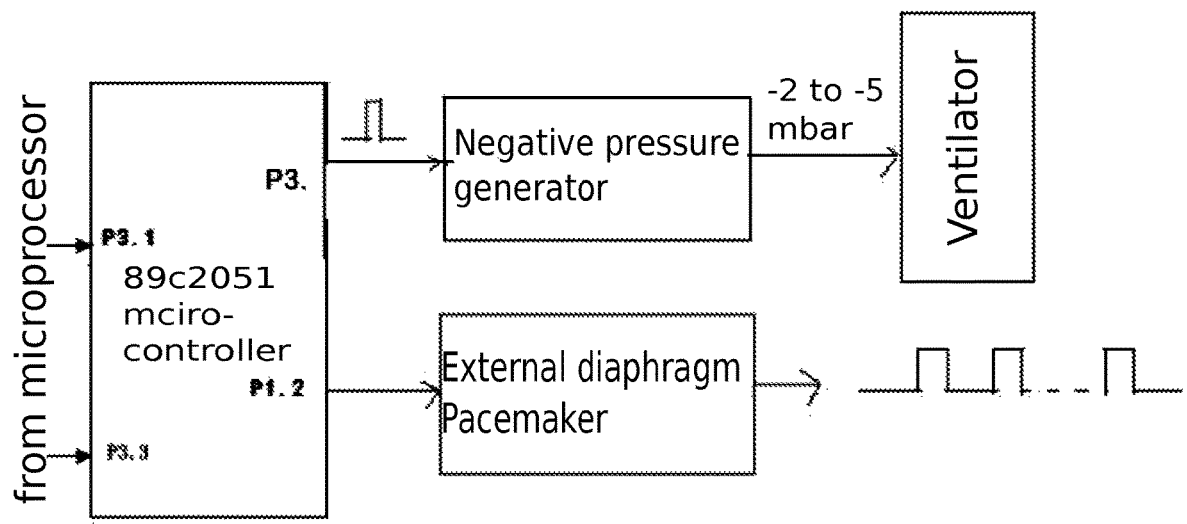
FIG. 5 is a diagram showing the microcontroller separately connected to the negative pressure generator and the external diaphragm pacemaker according to the present invention.
Figure 6:
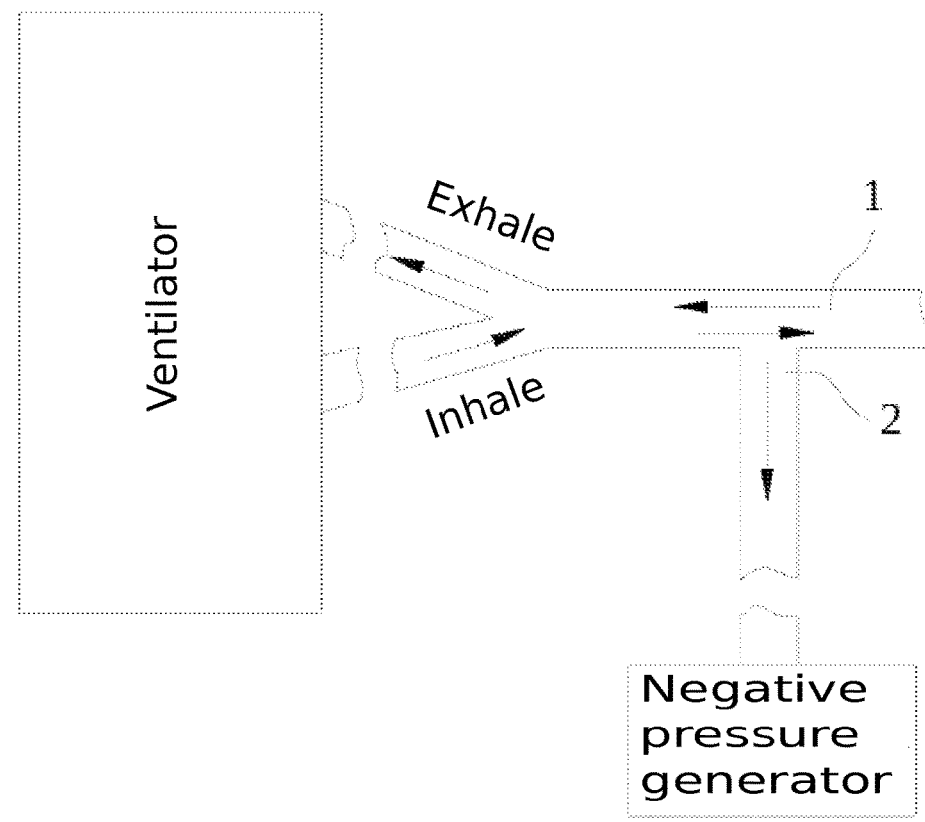
FIG. 6 is a diagram showing the connection between the negative pressure generator and the ventilator.

As shown in FIG. 4, this particular embodiment is also provided with a monitor and display driving circuit for displaying the operating status and the microprocessor has a monitor output terminal which is connected to the monitor via the display driving circuit. As shown in FIG. 6, the negative pressure generator is used to trigger the coupled operation of the ventilator. Specifically, when the negative pressure end 2 of the negative pressure generator is connected to the patient end 1 of the ventilator, it produces a negative pressure in the exhale-inhale tube, thereby creating an air flow which in turn triggers the operation of the ventilator. As shown in FIG. 5, the external diaphragm pacemaker of this embodiment has two output routes for outputting two routes of stimulus current. The stimulus current is of the following parameters: frequency 40 Hz, wave width 0.3 ms, and wave amplitude 0-120 V (adjusted automatically). The negative pressure generator is controlled by the microcontroller (Model 89C2051) via a triggering pulse, which triggers the generator to produce a negative pressure of 3-5 mbar. The negative pressure in turn triggers the ventilator into operation, either in an assisted ventilation mode or controlled ventilation mode so that the patient receiving the external pacemaking also receives mechanical ventilation support.

The microprocessor (chip model AT89C52) is the primary processor and the digital signal processor (chip model TMS320VC5416) is a secondary processor. The primary and second processors work together to complete tasks of EAdi collection, processing and analysis. In operation, the EAdi signal after being treated by TMS320VC5416 is outputted via its data ports (D0-D7) to AT89C52 via its input terminal P1-p7.

From the microprocessor, as shown in FIG. 4, the EAdi signal and the device's working status are outputted via port P2.0 to the monitor for display. The microcontroller (Model 89C2051) is another secondary processor to the microprocessor.

As shown FIG. 5, the control data to the external diaphragm pacemaker flow from microprocessor AT89C52's port P3.2 to microcontroller 89C2051's input port P3.1. In addition, the control signal to the negative pressure generator, as a unit pulse, flows from microprocessor AT89C52's port P3.4 to microcontroller 89C2051's input port P3.3. From the microcontroller, synchronized control signals are sent, on the one hand, from its port P3.2 to control the negative pressure generator and, on the other hand, from its port P1.2 to control the external ventilator, thereby realizing coupled operations between the ventilator and the external diaphragm pacemaker.

The present invention is not limited to the embodiment described above. A person of ordinary skill in the art may, according to the guidance described above and without departing from the basic principle of the present invention, make modifications, substitutions or changes in various forms, which can also achieve the object of the present invention.

What is claimed is:

1. A method of collaborating between external diaphragm pacemaking and mechanical ventilation comprising the following steps:
    (1) filtrating a captured EAdi (electrical activity of the diaphragm) signal mixed with interfering noises to obtain a treated EAdi signal;
    (2) evaluating an absolute peak value of the waveform of said treated EAdi signal and issuing a control action accordingly, wherein the absolute peak value of the waveform of said treated EAdi signal is referred to as a;
    (2.1) if a<0.5 µV, instructing an external diaphragm pacemaker to issue a stimulus current at a frequency of 10-12 beats per minute, and at the same time trigger a ventilator to perform ventilation in an assisted ventilation mode;
    (2.2) if 0.5≤a≤1.0 µV, instructing the external diaphragm pacemaker to issue a stimulus current at a frequency of 5-8 beats per minute, and at the same time trigger the ventilator to perform ventilation in an assisted ventilation mode;
    (2.3) if 1.0<a≤2.0 µV, instructing the external diaphragm pacemaker to issue a stimulus current at a frequency of 3-4 beats per minute and at the same time trigger the ventilator to perform ventilation in an assisted ventilation mode;
    (2.4) if there is no captured EAdi signal in the step (1), triggering the ventilator to perform ventilation in a controlled ventilation mode, that is, the ventilator to perform a backup ventilation function according to preset parameters, and instructing the external diaphragm pacemaker to issue an initial stimulus current at a frequency of 6-8 beats per minute;
    wherein after issuing the initial stimulus current by the diaphragm pacemaker, the current stimulation continues for a period of 30-40 minutes and then stops, such stimulation cycle being repeated 2-3 times within 24 hours and continued for each week with same stimulation cycles, and wherein during the intervals when the diaphragm pacemaker is not in operation, the ventilator maintains its operation according to regular operating parameters used in conventional clinical practice.

2. The method of collaborating between external diaphragm pacemaking and mechanical ventilation according to claim 1, wherein in steps (2.1) to (2.3) a negative pressure is used for a synchronized triggering of the ventilator, that is, a preset negative pressure generated by a negative pressure generator according to an assessment of the EAdi signal, which starts the operation of the ventilator in an assisted ventilation mode.

3. The method of collaborating between external diaphragm pacemaking and mechanical ventilation according to claim 1, wherein in steps (2.1) to (2.3) the ventilator is directly triggered by the EAdi signal, that is, a trigger signal is issued directly based on an assessment of the EAdi signal, which starts the operation of the ventilator in an assisted ventilation mode.

4. The method of collaborating between external diaphragm pacemaking and mechanical ventilation according to claim 1, further comprises a step of conducting a real time determination of t, which is defined as the time interval between peaks of two successive positive half waves or two successive negative half waves of the EAdi signal, and
    (a) if t<5 s, discarding the signal without sending stimulus current and without triggering the ventilator;
    (b) if 5s≤t≤10 s, returning to step (2) and determine the absolute peak value and the control action corresponding to the absolute peak value;
    (c) if t>10 s, executing the action described in step (2.4) as if no EAdi is captured.

5. The method of collaborating between external diaphragm pacemaking and mechanical ventilation according to claim 1, wherein in step (1), the EAdi signal mixed with interfering noises is subjected to the following filtering procedures sequentially: high-pass filtering, low-pass filtering, 50 Hz power frequency interference filtering and ECG wavelet filtering.

6. The method of collaborating between external diaphragm pacemaking and mechanical ventilation according to claim 4, wherein in step (1) the EAdi signal mixed with interfering noises is subjected to the following filtering procedures sequentially: high-pass filtering, low-pass filtering, 50 Hz power frequency interference filtering and ECG wavelet filtering.

7. A device coupling an external diaphragm pacemaking device to a ventilator, comprising an external diaphragm pacemaker, a negative pressure generator and an EAdi (electrical activity of the diaphragm) acquisition module for capturing EAdi signals from a diaphragm muscle, a signal processing module for treating the EAdi signals, and a microprocessor for analysis and assessment of the EAdi signals and a microcontroller for coupling control of the ventilator, wherein the negative pressure generator has a negative pressure generating terminal connected to the ventilator's end on a patient side and the EAdi acquisition module collects the EAdi signals, which are first treated by the signal processing module and then sent to the microprocessor for analysis and assessment, wherein based on the strength and time interval of two successive half-wave peaks of an EAdi signal of the EAdi signals, a corresponding control signal is sent to the microcontroller and the microcontroller outputs corresponding control signals which, on the one hand, trigger the external diaphragm pacemaker into operation and, on the other hand, trigger the operation of the negative pressure generator so that a negative pressure is generated in the negative terminal, which in turn triggers the operation of the ventilator.

8. The device according to claim 7, wherein said EAdi signal processing module comprises a signal amplifier, analog to digital converter and digital signal processor for filtering the EAdi signals, being successively connected in the order described, wherein the EAdi signals from the diaphragm outputted by the EAdi acquisition module are first amplified by the signal amplifier, then undergo conversion by the analog to digital converter, and finally filtered by the digital signal processor before being outputted.

9. The device according to claim 7, further comprising a display driver circuit and a monitor for displaying an operating state of the device, and said microprocessor has a display signal output terminal, which is connected to the monitor via the display driver circuit.

10. The method of collaborating between external diaphragm pacemaking and mechanical ventilation according to claim 2, further comprises a step of conducting a real time determination of t, which is defined as the time interval between peaks of two successive positive half waves or two successive negative half waves of the EAdi signal, and (a) if $t<5$ s, discarding the signal without sending stimulus current and without triggering the ventilator;

(b) if $5 \leq t \leq 10$ s, returning to step (2) and determine the absolute peak value and the control action corresponding to the absolute peak value;

(c) if $t>10$ s, executing the action described in step (2.4) as if no EAdi is captured.

11. The method of collaborating between external diaphragm pacemaking and mechanical ventilation according to claim 3, further comprises a step of conducting a real time determination of t, which is defined as the time interval between peaks of two successive positive half waves or two successive negative half waves of the EAdi signal, and (a) if $t<5$ s, discarding the signal without sending stimulus current and without triggering the ventilator;

(b) if $5 \leq t \leq 10$ s, returning to step (2) and determine the absolute peak value and the control action corresponding to the absolute peak value;

(c) if $t>10$ s, executing the action described in step (2.4) as if no EAdi is captured.

12. The method of collaborating between external diaphragm pacemaking and mechanical ventilation according to claim 2, wherein in step (1), the EAdi signal mixed with interfering noises is subjected to the following filtering procedures sequentially: high-pass filtering, low-pass filtering, 50 Hz power frequency interference filtering and ECG wavelet filtering.

13. The method of collaborating between external diaphragm pacemaking and mechanical ventilation according to claim 3, wherein in step (1), the EAdi signal mixed with interfering noises is subjected to the following filtering procedures sequentially: high-pass filtering, low-pass filtering, 50 Hz power frequency interference filtering and ECG wavelet filtering.

14. The device according to claim 8, further comprising a display driver circuit and a monitor for displaying an operating state of the device, and said microprocessor has a display signal output terminal, which is connected to the monitor via the display driver circuit.

* * * * *